United States Patent

Yang

[11] 4,006,138
[45] Feb. 1, 1977

[54] CRYSTALLINE FORM OF SODIUM O-FORMYLCEFAMANDOLE

[75] Inventor: Kuo S. Yang, Indianapolis, Ind.

[73] Assignee: Eli Lilly and Company, Indianapolis, Ind.

[22] Filed: Apr. 11, 1975

[21] Appl. No.: 567,324

[52] U.S. Cl. .......................... 260/243 C; 424/246
[51] Int. Cl.² .............................. C07D 501/60
[58] Field of Search ...................... 260/243 C

[56] References Cited

UNITED STATES PATENTS 3,641,021  2/1972  Ryan ..................... 260/243 C
3,887,551  6/1975  Crisp et al. ............. 260/243 C Primary Examiner—Nicholas S. Rizzo
Assistant Examiner—Jose Tovar
Attorney, Agent, or Firm—William B. Scanlon; Everet F. Smith

[57] ABSTRACT

The cephalosporin antibiotic, sodium 7-(D-α-formyloxy-α-phenylacetamido)-3-(1-methyl-1H-tetrazol-5-ylthiomethyl)-3-cephem-4-carboxylate, is provided in a stable, non-solvated anhydrate crystalline form designated as the gamma crystalline form.

1 Claim, 1 Drawing Figure

WATER SORPTION ISOTHERMS
CRYSTALLINE FORMS OF
O-FORMYLCEFAMANDOLE

*•SAMPLES DISSOLVED

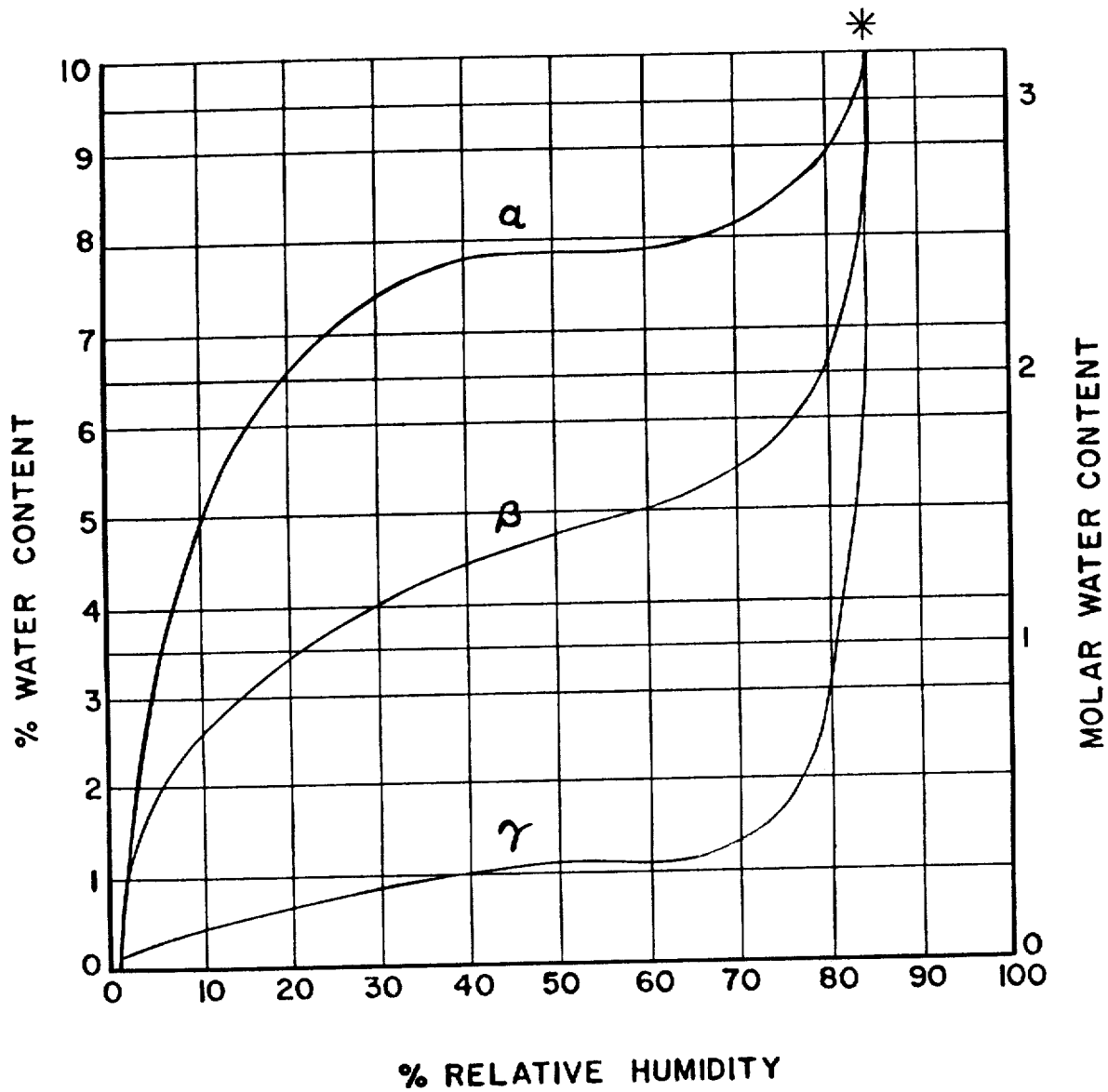

CRYSTALLINE FORM OF SODIUM O-FORMYLCEFAMANDOLE

BACKGROUND OF THE INVENTION

In U.S. Pat. No. 3,641,021 issued Feb. 8, 1972 Ryan describes the antibiotic, 7-D-mandelamido-3-(1-methyl-1,2,3,4-tetrazol-5-thiomethyl)-3-cephem-4-carboxylic acid known as cefamandole and the pharmaceutically acceptable salts thereof, for example the sodium salt. This antibiotic is highly effective in controlling the growth of both gram-positive and gram-negative microorganisms and is useful in the treatment of infectious diseases produced by gram-positive and gram-negative pathogens. This antibiotic as the free acid or in the form of the sodium salt has been difficult to obtain in a stable, dry form suitable for pharmaceutical formulations. However, the O-formyl ester derivative of the sodium salt form of the antibiotic, referred to herein as sodium O-formylcefamandole, is obtained in crystalline form suitable for formulations. This derivative, sodium 7-(D-α-formyloxy-α-phenylacetamido)-3-(1-methyl-1H-tetrazol-5-ylthiomethyl)-3-cephem-4-carboxylate, is likewise taught by Ryan as an intermediate useful in the preparation of cefamandole. The O-formyl ester derivative in in vitro testing inhibits the growth of gram-positive and gram-negative microorganisms at levels comparable to those observed with the parent cefamandole. In vivo studies with O-formylcefamandole demonstrate that the ester undergoes hydrolysis to a significant degree to provide the parent antibiotic cefamandole. Accordingly, the O-formyl ester provides a crystalline form suitable for preparing formulations for therapeutic use.

This invention relates to a new crystalline form of sodium 7-(D-α-formyloxy-α-phenylacetamido)-3-(1-methyl-1H-tetrazol-5-ylthiomethyl)-3-cephem-4-carboxylate. In particular this invention relates to a stable, non-solvated anhydrate crystalline form of O-formylcefamandole sodium salt.

SUMMARY OF THE INVENTION

Sodium O-formylcefamandole is obtained in a non-solvated, anhydrate crystalline form designated the gamma-form, by diluting a solution of the salt in a solvent such as a methanol with an anti-solvent such as isopropanol under substantially anhydrous conditions to induce crystallization. The gamma-crystalline form exhibits a high degree of stability under conditions of high relative humidity.

DETAILED DESCRIPTION

Sodium 7-(D-α-formyloxy-α-phenylacetamido)-3-(1-methyl-1H-tetrazole-5-ylthiomethyl)-3-cephem-4-carboxylate referred to herein as sodium O-formylcefamandole is represented by the following structural formula.

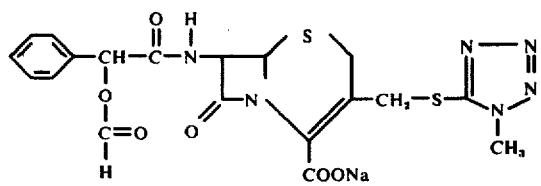

The antibiotic sodium salt has been previously obtained in two identifiable crystalline forms. The first of these forms, the α-form, melts at about 184°–5° C. and is a solvated (acetone) crystalline form. The second crystalline form, the β-form, melts at about 165° C. and is a hydrated form. These crystalline forms are undesirable for use in pharmaceutical formulations primarily because both have a relatively high affinity for atmospheric moisture which leads to instability in the solid state. In addition to its affinity for moisture the α-form is solvated with acetone. Acetone is an undesirable contaminant in any parenteral pharmaceutical preparation. Attempts to remove the acetone with retention of crystallinity have been unrewarding.

The novel crystalline form of sodium O-formylcefamandole provided by this invention is designated the γ (gamma) form. It has a melting point of $190° \pm 1°$ C (capillary). The γ-form is obtained as a colorless white solid which appears as small birefringent needles under the polarizing microscope.

The γ-crystalline form is characterized by its X-ray powder diffraction pattern. Using nickel-filtered copper radiation (Cu:Ni) at a wave length of $\gamma = 1.5405 A$ to calculate the interplanar spacings (d) the following relative intensity readings ($I/I_1$) were obtained.

| d | $I/I_1$ |
|---|---|
| 17.80 | .30 |
| 11.76 | .30 |
| 9.39 | .10 |
| 7.49 | .70 |
| 7.18 | .20 |
| 6.20 | .15 |
| 5.52 | .40 |
| 5.00 | .40 |
| 4.74 | .20 |
| 4.54 | .80 |
| 4.20 | .50 |
| 3.98 | .10 |
| 3.72 | 1.00 |
| 3.51 | .05 |
| 3.32 | .02 |
| 3.06 | .10 |
| 2.91 | .15 |
| 2.83 | .15 |
| 2.75 | .10 |
| 2.56 | .05 |
| 2.36 | .10 |
| 2.17 | .10 |
| 2.11 | .10 |

The γ-form, in contrast to the α- and β-forms, exhibits a low affinity for atmospheric moisture. Because of its low tendency to adsorb moisture the γ-crystalline form possesses greater solid state stability which is important in the handling and storage of bulk quantities of the antibiotic salt. Further, the γ-form's low affinity for moisture provides for longer shelf life in the solid state.

The low moisture affinity of the γ-form in comparison to the moisture affinities of the α- and β-forms is shown graphically by the water sorption isotherms in the accompanying drawing. As shown, the γ-form absorbs only about one percent by weight of water when exposed to a relative humidity of up to about 60–70% at a temperature of about 25° C. In the same range of relative humidity the α form absorbs between about 8 and 9% by weight of water and the α-form (hydrated) absorbs between about 5 and 5.5% by weight of water.

The γ-crystalline form of O-formylcefamandole is obtained by diluting a solution of the salt in a suitable organic solvent with an antisolvent under substantially anhydrous conditions.

Suitable solvents which can be used in the crystallization of the γ-form are selected from the relatively polar organic solvents in which the O-formylcefamandole sodium salt is soluble in appreciable amounts. Alcoholic solvents such as methanol and ethanol can be used as well as the more polar solvents, formamide, dimethylformamide, dimethylacetamide and dimethylsulfoxide.

The term "antisolvent" as used herein refers to organic solvents in which the salt is not appreciably soluble and generally are of lower polarity than the solvent used to effect solution of the O-formylcefamandole sodium salt. Antisolvents which can be used are, for example, isopropanol, acetonitrile, propionitrile, butyronitrile, diethyl ether, acetone, methylethyl ketone and diethyl ketone. The antisolvents employed in the crystallization are miscible with the solvents used to solubilize the salt.

Desirable solvent-antisolvent combinations useful for preparing the γ-crystalline form include, for example, methanol-isopropanol, dimethylacetamide-acetonitrile and dimethylformamide-isopropanol.

In carrying out the crystallization of the γ-form it is preferable, although not necessary, to use a concentrated solution of sodium O-formylcefamandole. Dilute solutions of the salt require larger volumes of the antisolvent to induce crystallization. Large volumes of both the solvent and antisolvent are undesirable in large scale manufacturing operations.

Mixtures of solvents can also be used to prepare solutions of the O-formylcefamandole sodium salt. Concentrated solutions of the salt in polar solvents such as dimethylformamide or dimethylacetamide require large volumes of antisolvents to induce crystallization of the γ-form. Accordingly it is desirable to use mixtures of the polar solvent with less polar solvents to prepare the salt solution to avoid the use of a large amount of antisolvent. For example, a concentrated solution of the salt can be prepared in a mixture of dimethylformamide and acetonitrile and the γ-form precipitated by diluting the solution with the antisolvent isopropanol.

The crystallization of the γ-form can be carried out at a temperature between about 0° and 65° C. however it is conveniently carried out at about 20° to 25° C.

The crystallization is performed with solvents and antisolvents which are substantially dry. Reagent grade solvents are preferable although not required for successful crystallizations of high yield. Certain amounts of water can be tolerated in the crystallization, however the amount of water present should be kept to a minimum to avoid formation of the hydrated β-crystalline form.

The sodium O-formylcefamandole employed in the crystallization to obtain the γ-form can be in any solid state. For example, amorphous, semi-crystalline, or α- or β-crystalline forms can be used. Alternatively, γ-form sodium O-formylcefamandole can be crystallized from a mixture of the free acid form of O-formylcefamandole and sodium 2-ethylhexanoate in a solvent-antisolvent combination such as acetone-isopropanol (1.25:1 v:v).

As previously mentioned the γ-crystalline form is non-hydrated and has a low affinity for atmospheric moisture under conditions of high relative humidity. This property affords solid state stability which is superior to that of the hydrated β-form. The water present in the β-crystalline form can promote the hydrolysis of the O-formyl ester in the solid state thus leading to instability even at low relative humidity.

Accordingly the γ-crystalline form is especially useful in preparing stable, dry state formulations useful for parenteral administration. For example, it can be formulated into dosage units with sodium carbonate or with tris(hydroxymethyl)aminomethane (tris-buffer) which upon dilution with sterile water afford clear solutions for intramuscular injection or for intravenous administration.

The following examples are provided to further illustrate this invention and are not to be construed as limitations thereof.

The synthesis of O-formylcefamandole free acid and its conversion to the α-crystalline form is described by Example 1. Examples 2 and 3 describe crystallization procedures for obtaining the γ-form of sodium O-formylcefamandole with representative solvent-antisolvent combinations.

EXAMPLE 1

Preparation of Sodium 7-(D-2-formyloxy-2-phenylacetamido)-3-(1-methyl-1H-tetrazol-5-ylthiomethyl)-3-cephem-4-carboxylate.

To 21.6 kg. (17.8 l.) of 98 percent formic acid was added 1.14 kg. (7.5 M) of D-(-)-mandelic acid and the reaction mixture was heated for 4 hours at 70° C. with stirring. The excess formic acid was evaporated off in vacuo and the residual syrup was dissolved in 6 l. of benzene. The solution was washed twice with 6 l. portions of water and was dried over magnesium sulfate. The drying agent was filtered and washed with 1.5 l. of benzene, the washes being added to the filtrate. The dried filtrate was evaporated in vacuo to obtain the D-(-)-mandelic acid formate ester as a syrup. The product can be crystallized from cyclohexane to yield material melting at about 55°–58° C.

The mandelic acid formate ester obtained as a syrup as described above is stirred for 2 hrs. with 2.9 kg. (ca. 1.75 l.) of thionyl chloride at a temperature of about 70° C. The excess thionyl chloride is removed by evaporation and the residual green solution is vacuum distilled. The product, O-formyl mandeloyl chloride, distills over at 127°–130° C. (15 mm.) or at 108°–112° C. (7 mm.). Specific rotation $[\alpha]_D^{25°}$ − 175°

Elemental Analysis for $C_9H_7ClO_3$: Calculated: C, 54.42; H, 3.55; Cl, 17.85. Found: C, 54.17; H, 3.48; Cl, 17.95.

To 13 l. of ethyl acetate were added 851.1 g. (2.59 M) of 7-amino-3-(1-methyl-1H-tetrazol-5-ylthiomethyl)-3-cephem-4-carboxylic acid and 1,361 g. (10.37 M) of monotrimethylsilyl acetamide, and the mixture was stirred at 50° C. until a clear solution was obtained. The solution was cooled to 20° C. and 514 g. (2.59 M) of O-formyl mandeloyl chloride was added at a rate such that the temperature of the reaction solution was maintained between about 20°–25° C. with ice-cooling. The reaction mixture was stirred for 1.5 hours at about room temperature after the addition of the mandeloyl chloride was completed. Five liters of water were then added to the reaction mixture and the diluted mixture was stirred for about 10 minutes. The organic layer was separated and was washed twice with water. The combined washes are extracted with 1.5 l. of ethyl acetate and the extract is combined with the washed organic layer. The whole was dried over magnesium sulfate, filtered and evaporated in vacuo on a 25° C. water bath to yield 1,460 g. of product, 7-(D-2-formyloxy-2-phenylacetamido)-3-(1-methyl-1H-tetrazol-5-ylthiomethyl)-3-cephem-4-carboxylic acid, as a yellow foam.

The product was dissolved in 5 l. of acetone and the solution was mixed with a solution of 430 g. (2.59 M) of sodium 2-ethylhexanoate in 5.4 l. of acetone. The combined solutions were seeded and stirred in an ice bath for 1.5 hours. The crystalline precipitate of sodium 7-(D-2-formyloxy-2-phenylacetamido)-3-(1-methyl-1H-tetrazol-5-ylthiomethyl-3-cephem-4-carboxylate was filtered and washed with 5 l. of acetone. The crystalline salt was dried overnight in a vacuum oven at 40° C. to yield 1,060 g. (80%) of product melting at about 182°–184° C. U.V. absorption: $E_1{}_{cm}{}^{1\%}$ (ethanol 208. Nuclear magnetic resonance spectrum: (D$_2$O) δ3.40 (d, 2H); δ3.94 (s, tetrazole 1-methyl group); δ4.15 (s, —CH$_2$—S); δ4.94 (d, 6H); δ5.63 (d, 7H), δ6.20 (s, benzylic H); δ7.40 (m, C$_6$H$_5$); δ8.25 (s, CHO) and δ8.87 (d, NH).

EXAMPLE 2

Ten grams of sodium O-formylcefamandole were dissolved in 200 ml. of anhydrous methanol and the solution was filtered to remove undissolved particles. To the clear solution, anhydrous isopropyl alcohol was slowly added with stirring until the solution became turbid. The cloudy solution was allowed to stand undisturbed for 4 hours while crystallization of the δ-form proceeded.

The crystals were collected by filtration and were washed with a mixture of anhydrous methanol and anhydrous isopropyl alcohol. The product was dried at 40° C. under vacuum for about 4 hours. The dried crystals melted at about 190° C. and were obtained in a 75% yield.

EXAMPLE 3

A concentrated solution of O-formylcefamandole (β-form) in dimethylformamide was stirred at about 20° C. while dry acetonitrile was added dropwise to the turbidity point. The solution was allowed to stand undisturbed while crystallization of the δ-form progressed over 4 hours. The precipitate was filtered and was washed with acetonitrile and dried in vacuo at about 45° C.

EXAMPLE 4

Preparation of δ-form Sodium O-Formylcefamandole with O-formylcefamandole Free Acid and Sodium 2-ethylhexanoate.

To a solution of 18.82 g. of O-formylcefamandole free acid in acetone-isopropanol (1:1, v:v) was added dropwise with stirring at 24° C. a solution of 6.64 g of sodium 2-ethylhexanoate in 40 ml of 1:1 acetone-isopropanol. The solution was stirred for 2 hours and the white precipitate of the γ-form sodium O-formylcefamandole was filtered. The salt was washed with 50 ml. of 1:1 acetone-isopropanol and dried overnight in vacuo at about 45° C. The product weighed 16.62 g. (88.3% yield) after drying.

I claim:
1. The crystalline anhydrate form of the compound of the formula

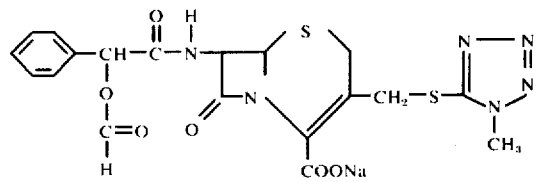

which has a melting point of 190°±1° C. and which has the following X-ray powder diffraction pattern obtained with nickel filtered copper radiation of γ1.5405 wherein d represents the interplanar spacings and I/I$_1$ the relative intensities:

| d | I/I$_1$ |
|---|---|
| 17.80 | .30 |
| 11.76 | .30 |
| 9.39 | .10 |
| 7.49 | .70 |
| 7.18 | .20 |
| 6.20 | .15 |
| 5.52 | .40 |
| 5.00 | .40 |
| 4.74 | .20 |
| 4.54 | .80 |
| 4.20 | .50 |
| 3.98 | .10 |
| 3.72 | 1.00 |
| 3.51 | .05 |
| 3.32 | .02 |
| 3.06 | .10 |
| 2.91 | .15 |
| 2.83 | .15 |
| 2.75 | .10 |
| 2.56 | .05 |
| 2.36 | .10 |
| 2.17 | .10 |
| 2.11 | .10 |

* * * * *